United States Patent
Lin et al.

(10) Patent No.: US 6,238,657 B1
(45) Date of Patent: *May 29, 2001

(54) OIL-IN-OIL AND THREE-PHASE EMULSIONS

(75) Inventors: Zuchen Lin; William James Schulz, Jr., both of Midland; Janet Mary Smith, Bay City, all of MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/352,006

(22) Filed: Jul. 12, 1999

(51) Int. Cl.[7] ............................... A61K 7/32; A61K 6/00; A61K 7/06; C08G 77/06; C08J 83/02
(52) U.S. Cl. .................................. 424/70.12; 424/70.11; 424/401; 424/78.02; 424/65; 524/861; 524/862; 528/15
(58) Field of Search ............................ 424/401, 65, 70.1, 424/70.11, 78.02, 70.12; 524/861, 862; 528/15

(56) References Cited

U.S. PATENT DOCUMENTS

| | | | |
|---|---|---|---|
| 4,853,474 | * | 8/1989 | Bahr et al. . |
| 5,136,068 | * | 8/1992 | Bahr et al. . |
| 5,456,906 | * | 10/1995 | Powell et al. . |
| 5,654,362 | * | 8/1997 | Schulz, Jr. et al. . |
| 5,811,487 | * | 9/1998 | Schulz, Jr. et al. . |
| 5,880,210 | * | 3/1999 | Schulz, Jr. et al. . |
| 5,889,108 | * | 3/1999 | Zhang . |

FOREIGN PATENT DOCUMENTS

97/17938  5/1997  (WO) .

OTHER PUBLICATIONS

Journal of Colloid and Interface Science, vol. 195, pp. 101–113, Article No. CS975158, Jan. 1, 1997.

* cited by examiner

*Primary Examiner*—Thurman K. Page
*Assistant Examiner*—Brian K. Seidleck
(74) *Attorney, Agent, or Firm*—James L. DeCesare

(57) ABSTRACT

Three-dimensional silicone elastomers having polyether and higher alkyl functionality in their molecules form networks of crosslinked linear siloxanes with polyether and olefin containing repeating units, and these silicone elastomers can be used as emulsifiers for making O/O and three-phase aqueous emulsions. One of the oil phases is a silicone oil, while the other oil phase is an organic oil such as mineral oil or castor oil. These emulsions of two and three mutually insoluble liquids are useful in personal and health care applications.

12 Claims, No Drawings

OIL-IN-OIL AND THREE-PHASE EMULSIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to oil-in-oil (O/O) emulsions and to certain three-phase emulsions prepared with an emulsifier which is an elastomeric polyorganosiloxane containing four different types of difunctional "D" units $R_2SiO_{2/2}$. The elastomeric polyorganosiloxane is a polymer with (i) dimethyl, (ii) higher alkyl, (iii) polyether, and (iv) crosslinking groups.

BACKGROUND OF THE INVENTION

Emulsions are disperse systems consisting of two or more mutually insoluble or sparingly soluble liquids. The liquid usually present in excess is termed the continuous or external phase, while the liquid dispersed in it is termed the dispersed or internal phase.

If the external phase consists of water, and the internal phase consists of an organic liquid, i.e., mineral oil, the term oil-in-water (O/W) emulsion is used. If water is finely dispersed in a nonaqueous liquid, a water-in-oil (W/O) emulsion is produced. If two nonaqueous liquids are emulsified in each other, the term oil-in-oil (O/O) emulsion is used.

The term three-phase emulsion is used herein to describe a system of three mutually insoluble liquids which are emulsified simultaneously. Technically, it is not what is commonly referred to as a multiple emulsion, in which only two mutually insoluble liquids are present. For example, in the three-phase emulsion of the present invention, an organic oil and water are emulsified into a silicone oil continuous phase, although all three of the liquids are otherwise mutually insoluble one in the other.

While O/W and W/O emulsions containing a silicone oil are common, O/O emulsions in which at least one of the phases is a silicone oil are quite rare. Reference may be had, for example, to the *Journal of Colloid and Interface Science*, Volume 195, Pages 101–113, Article No. CS975158, Jan. 1, 1997, which describes certain paraffin oil-in-silicone oil O/O emulsions, as well as certain silicone oil-in-paraffin oil O/O emulsions.

Quite unexpectedly, it has now been found that one skilled in the art is enabled to readily prepare silicone oil containing O/O emulsions, as well as three-phase emulsions, using as the emulsifier, an elastomeric silicone polymer according to the present invention. While the elastomeric silicone polymer contains polyether groups which are characteristic of many organic emulsifiers, it is also a three-dimensional molecular polymeric network consisting of tens, hundreds, and even thousands of crosslinking units between and among its polymeric molecules, and therefore one would not normally expected it to function as an emulsifier in a nonaqueous system such as an O/O emulsion. It is also unexpected that a single emulsifier could be used to form both O/O emulsions and three-phase emulsions.

In comparison to silicone polyether emulsifiers, i.e., glycol modified siloxanes, which are not crosslinked molecules, an additional unexpected benefit of using a crosslinked elastomeric silicone polymer as emulsifier for three-phase emulsions, is that it is capable of thickening the external silicone oil phase of the emulsion. This eliminates the need of separate thickening agents in order to achieve the desired viscosity of the final emulsion. It also eliminates the need of using high internal phases, i.e., where the amount of internal phase exceeds the amount of external phase, to achieve the same result as in WO 97/17938 (May 22, 1997), for example.

BRIEF SUMMARY OF THE INVENTION

This invention, therefore, relates to a nonaqueous oil-in-oil emulsion containing a silicone oil as one phase of the emulsion, and an organic oil as the other phase of the emulsion.

The emulsifier used to form the O/O emulsion is an elastomeric silicone polymer prepared by combining and reacting (A) an ≡Si—H containing polysiloxane, (B) a mono-alkenyl polyether, (C) an α-olefin containing at least ten carbon atoms, (D) an α,ω-unsaturated hydrocarbon such as an α,ω-diene, α,ω-diyne, or an α,ω-ene-yne, in the presence of (E) an oil, and (F) a platinum catalyst, until a silicone elastomer is formed by crosslinking and addition of ≡SiH across double or triple bonds in the α,ω-unsaturated hydrocarbon. The reaction is allowed to continue until there is formed a crosslinked three-dimensional gelled network of the elastomeric silicone polymer containing or swollen by oil (E).

The invention also relates to certain three-phase aqueous emulsions prepared from such O/O emulsions. These O/O and three-phase emulsions may additionally contain other oil-soluble as well as water-soluble active ingredients in a respective one of the oil or water phases.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The elastomeric silicone polymer used to prepare the O/O emulsions and the three-phase emulsions of this invention, and its method of preparation, are described in detail in copending application U.S. Ser. No. 09/299,864, filed on Apr. 28, 1999, entitled "Elastomeric Silicone Terpolymer". The copending application is assigned to the same assignee as the present application.

One preferred method for preparing the polymer as described in the copending application is illustrated below, although the polymer can be prepared by other methods using other sequences of steps:

Step 1: Incorporation of the Polyether

≡SiH siloxane+mono-alkenyl polyether+Pt catalyst→≡SiH siloxane with polyether groups Step 2: Incorporation of the α-Olefin

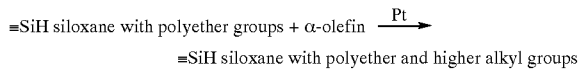

≡SiH siloxane with polyether and higher alkyl groups

Step 3: Gelation
≡SiH siloxane with polyether and higher alkyl groups+ ≡SiH siloxane (optional)+α,ω-unsaturated hydrocarbon+oil(s)+Pt catalyst→gel/elastomer containing the oil(s)
Step 4: Shearing & Swelling—Optional
gel/elastomer+oil(s)+active ingredient→paste An O/O emulsion and a three-phase emulsion according to the present invention can then be prepared as shown below:
Step 5: Emulsification/Preparation of O/O Emulsion
silicone gel/elastomer/paste+oil(s)+active ingredient+ shear→O/O Emulsion
Step 6: Preparation of a Three-Phase Emulsion
O/O Emulsion+$H_2O$+shear→Three-Phase Emulsion The ≡Si—H siloxane is represented by compounds of the formula $R_3SiO(R'_2SiO)_a(R''HSiO)_bSiR_3$, compounds of the formula $HR_2SiO(R'_2SiO)_cSiR_2H$, or compounds of the formula $HR_2SiO(R'_2SiO)_a(R''HSiO)_bSiR_2H$. Mixtures of these types of compounds can also be employed. In the three formulas, R, R', and R", are alkyl groups with 1–6 carbon atoms; a is 0–250; b is 1–250; and c is 0–250.

The ≡Si—H containing polysiloxane can also comprise an alkylhydrogen cyclosiloxane or an alkylhydrogen-dialkyl cyclosiloxane copolymer, represented in general by the formula $(R'_2SiO)_{a'}(R''HSiO)_{b'}$, where R' and R" are as defined above, and where a' is 0–7 and b' is 3–10. Some representative compounds of these types are $(OSiMeH)_4$, $(OSiMeH)_3(OSiMeC_6H_{13})_3$, $(OSiMeH)_2(OSiMeC_6H_{13})_2$, and $(OSiMeH)(OSiMeC_6H_{13})_3$, where Me represents methyl.

The most preferred α,ω-unsaturated hydrocarbon is an α,ω-diene of the formula $CH_2=CH(CH_2)_dCH=CH_2$ where d is 1–20. Some representative examples of suitable α,ω-dienes are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

Other α,ω-unsaturated hydrocarbons can also be used such as α,ω-diynes of the formula $CH≡C(CH_2)_eC≡CH$; or α,ω-ene-ynes of the formula $CH_2=CH(CH_2)_eC≡CH$ where e is 0–20. Some representative examples of suitable α,ω-diynes are 1,3-butadiyne HC≡C—CH≡CH and 1,5-hexadiyne (dipropargyl) HC≡C—$CH_2CH_2$—C≡CH. One example of a suitable α,ω-ene-yne is hexene-5-yne-1 $CH_2$=CH$CH_2CH_2$C≡CH.

A catalyst is needed to effect the reaction between the ≡SiH containing siloxane, the mono-alkenyl polyether, the α-olefin, and the α,ω-unsaturated hydrocarbon. Suitable catalysts are Group VIII transition metals, i.e., the noble metals. The preferred catalyst is a platinum divinyl tetramethyl disiloxane complex carried in a silicone fluid or solvent which is described by Karstedt in his U.S. Pat. Nos. 3,715,334 and 3,814,730.

The mono-alkenyl polyether is a compound of the formula $CH_2=CH(CH_2)_fO(CH_2CH_2O)_g(CH_2CH_3CHO)_hT$, or a compound of the formula $CH_2=CH—Q—O(CH_2CH_2O)_g(CH_2CH_3CHO)_hT$. In the formulas, T represents an end group which can be hydrogen; a C1–C10 alkyl group such as methyl, ethyl, propyl, butyl, and decyl; an aryl group such as phenyl; or a C1–C20 acyl group such as acetyl, propionyl, butyryl, lauroyl, myristoyl, and stearoyl. Q is a divalent linking group containing unsaturation such as phenylene —$C_6H_4$—. The value of f is 0–6; g has a value of 4–100; and h can be zero or have a value of 1–100.

The α-olefin is a compound of the formula $CH_2=CHR'''$ where R''' is a higher alkyl group containing 8–40 carbon atoms. Some representative examples of suitable α-olefins are 1-decene ($C_{10}$), 1-undecene, 1-dodecene, 1-tridecene, 1-tetradecene, 1-pentadecene ($C_{15}$), 1-hexadecene, 1-octadecene, 1-nonadecene, 1-eicosene ($C_{20}$), 1-heptacosene, and α-olefin fractions containing various amounts of $C_{22}$-$C_{30+}$ α-olefins sold under the trademark GULFTENE® 24-28 and GULFTENE® 30+ by the Chevron Chemical Company, Houston, Tex.

Silicone oils suitable for use in making O/O emulsions and three-phase emulsions according to this invention include both volatile and nonvolatile, preferably low molecular weight, linear and cyclic methyl, higher alkyl, or aryl siloxanes.

The volatile linear methyl siloxanes have the formula $(CH_3)_3SiO\{(CH_3)_2SiO\}_kSi(CH_3)_3$. The value of k is 0–5. The volatile cyclic methyl siloxanes have the formula $\{(CH_3)_2SiO\}_m$. The value of m is 3–9. Preferably, these volatile polydimethylsiloxanes have a boiling point less than about 250° C. and viscosity of about 0.65 to about 5.0 $mm^2/s$.

Some representative volatile linear methyl siloxanes are hexamethyldisiloxane (MM) with a boiling point of 100° C., viscosity of 0.65 $mm^2/s$, and formula $Me_3SiOSiMe_3$; octamethyltrisiloxane (MDM) with a boiling point of 152° C., viscosity of 1.04 $mm^2/s$, and formula $Me_3SiOMe_2SiOSiMe_3$; decamethyltetrasiloxane ($MD_2M$) with a boiling point of 194° C., viscosity of 1.53 $mm^2/s$, and formula $Me_3SiO(Me_2SiO)_2SiMe_3$; dodecamethylpentasiloxane ($MD_3M$) with a boiling point of 229° C., viscosity of 2.06 $mm^2/s$, and formula $Me_3SiO(Me_2SiO)_3SiMe_3$; tetradecamethylhexasiloxane ($MD_4M$) with a boiling point of 245° C., viscosity of 2.63 $mm^2/s$, and formula $Me_3SiO(Me_2SiO)_4SiMe_3$; and hexadecamethylheptasiloxane ($MD_5M$) with a boiling point of 270° C., viscosity of 3.24 $mm^2/s$, and formula $Me_3SiO(Me_2SiO)_5SiMe_3$.

Some representative volatile cyclic methyl siloxanes are hexamethylcyclotrisiloxane ($D_3$) a solid with a boiling point of 134° C. and formula $\{(Me_2)SiO\}_3$; octamethylcyclotetrasiloxane ($D_4$) with a boiling point of 176° C., viscosity of 2.3 $mm^2/s$, and formula $\{(Me_2)SiO\}_4$; decamethylcyclopentasiloxane ($D_5$) with a boiling point of 210° C., viscosity of 3.87 $mm^2/s$, and formula $\{(Me_2)SiO\}_5$; and dodecamethylcyclohexasiloxane ($D_6$) with a boiling point of 245° C., viscosity of 6.62 $mm^2/s$, and formula $\{(Me_2)SiO\}_6$.

The nonvolatile linear and cyclic higher alkyl and aryl siloxanes are represented respectively by the formulas $Ra_3SiO(R^a_2SiO)_nSi^{Ra}_3$ and $(R^a_2SiO)_p$. $R^a$ can be an alkyl group with 1–20 carbon atoms, or an aryl group such as phenyl. $R^a$ can also be an aralkyl (arylalkyl) group such as benzyl, or an alkaryl (alkylaryl) group such as tolyl. The value of n is 0–80, preferably 5–20. The value of p is 3–9, preferably 4–6. These polysiloxanes generally have a viscosity in the range of about 5–100 $mm^2/s$.

Polysiloxanes can also be used where n has a value sufficient to provide siloxane polymers with a viscosity in the range of about 100–1,000 $mm^2/sec$. Typically, n can be about 80–375. Illustrative of such polysiloxanes are polydimethylsiloxane, polydiethylsiloxane, polymethylethylsiloxane, polymethylphenylsiloxane, and polydiphenylsiloxane.

Generally, therefore, the silicone oil can have a viscosity of about 0.65 to about 1,000 $mm^2/s$.

As noted above, the oil-in-oil emulsion and the three-phase emulsion contain an organic oil as one phase of the emulsion. By organic oil is meant, generally, a natural oil that is derived from an animal, a vegetable, or a mineral source.

Modern cosmetic oils are most representative of the organic oil, and among the more common organic oils known to be safe for cosmetic purposes are almond oil, apricot kernel oil, avocado oil, cacao butter (theobroma oil), carrot oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark oil, soybean oil, sweet almond oil, tallow (beef) oil, tallow (mutton) oil, turtle oil, vegetable oil, whale oil, and wheat germ oil.

Useful active ingredients which may be used include both fat or oil-soluble vitamins for inclusion in an oil phase of the O/O emulsion, as well as water-soluble vitamins for inclusion in the water in the three-phase emulsion.

Oil-soluble vitamins useful herein include, but are not limited to, Vitamin $A_1$, RETINOL, $C_2$-$C_{18}$ esters of RETINOL, vitamin E, TOCOPHEROL, esters of vitamin E, and mixtures thereof. RETINOL includes trans-RETINOL, 13-cis-RETINOL, 11-cis-RETINOL, 9-cis-RETINOL, and 3,4-didehydro-RETINOL. The oil-soluble vitamin can be used in amounts of from 0.01 to about 50 percent by weight.

RETINOL is the International Nomenclature Cosmetic Ingredient Name (INCI) of The Cosmetic, Toiletry, and Fragrance Association (CTFA), Washington DC, for vitamin A. Accordingly, other suitable oil-soluble vitamins which can be included are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Water-soluble vitamins useful herein include, but are not limited to, Vitamin C, Vitamin $B_1$, Vitamin $B_2$, Vitamin $B_6$, Vitamin $B_{12}$, niacin, folic acid, biotin, and pantothenic acid. Other suitable water-soluble vitamins by INCI name are ASCORBYL DIPALMITATE, ASCORBYL METHYLSILANOL PECTINATE, ASCORBYL PALMITATE, and ASCORBYL STEARATE. The water-soluble vitamin, like the oil-soluble vitamin, can be used in amounts of from 0.01 to about 50 percent by weight.

Other types of active ingredients may also be used such as water-soluble or oil-soluble drugs. Representative examples of some suitable water-soluble drugs which can be included in water of the three-phase emulsion are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole.

Representative examples of some suitable oil-soluble drugs which can be included in an oil of the O/O emulsion or the three-phase emulsion are clonidine, scopolamine, propranolol, estradiol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Other materials considered drugs and which can be used are antiacne agents such as benzoyl peroxide, triclosan, and tretinoin; antibacterial agents such as chlorohexadiene gluconate; antifungal agents such as miconazole nitrate; anti-inflammatory agents such as salicylic acid; corticosteroidal drugs; non-steroidal anti-inflammatory agents such as diclofenac; antipsoriasis agents such as clobetasol propionate and retinoids; anesthetic agents such as lidocaine; antipruritic agents; antidermatitis agents; and agents generally considered barrier films.

The process for making the O/O emulsion is carried out by combining the elastomeric silicone polymer and the oils, and mixing the ingredients at room temperature until an O/O emulsion is formed. Shear force is used to form the O/O emulsion. Any type of mixing and shearing equipment may be used to perform these steps such as a batch mixer, planetary mixer, single or multiple screw extruder, dynamic or static mixer, colloid mill, homogenizer, sonolator, or a combination thereof.

For example, to form an O1/O2 emulsion, it is preferred to use 0.1 to 99 percent by weight of an organic oil as the O1 phase which includes the amount of any oil-soluble active ingredient such as a vitamin(s) contained therein. A silicone oil is used as the O2 continuous phase in an amount of about 1 to 99.9 percent by weight including the elastomeric silicone polymer, any other oil(s), oil-soluble vitamin(s), or fat-soluble active ingredients contained therein.

A three-phase emulsion can then be prepared by mixing together about 0.1 to 70 percent by weight of the O1/O2 emulsion, and about 30 to 99.9 percent by weight of water including any water-soluble ingredient(s) contained in the water. One advantage of the three-phase emulsion is that it is capable of simultaneously housing fat and water-soluble active ingredients side by side in the oil(s) and aqueous phases of the emulsion, respectively.

EXAMPLES

The following examples illustrate this invention in more detail.

Example 1
Process for Making Elastomeric Silicone Polymers

In this example, an ESCO EL-1 processor mixer was employed. The processor mixer was equipped with a one liter jacketed glass container having heating and cooling capability, an anchor sweep blade with speed control settings of 20–300 rpm (2–31 rad/s), a high speed homogenizer with Cowles type blades, speed controls for 750–15,000 rpm (78–1,570 rad/s) operation, a temperature gauge, a product inlet, a vacuum connection, and a circulation bath with heating and cooling capacity.

The following materials were used to prepare two elastomeric silicone polymers A and B according to the procedure explained below:

1. The ≡SiH siloxane was a copolymer generally corresponding to the formula $Me_3SiO(Me_2SiO)_{77}(MeHSiO)_{20}SiMe_3$ in which Me represents methyl. There are twenty (20) reactive sites available in the copolymer for reaction or crosslinking. Reference may be had to Table 1 with respect to how these twenty sites were consumed.

2. The α,ω-unsaturated hydrocarbon was 1,5-hexadiene.

3. The mono-alkenyl polyethers had a chain length of 7 and 12, respectively, and were compositions corresponding to the general formulas $CH_2$=$CH(CH_2)O(CH_2CH_2O)_7H$ and $CH_2$=$CH(CH_2)O(CH_2CH_2O)_{12}H$.

4. The oil consisted of cyclic siloxane $D_5$, i.e., decamethylcyclopentasiloxane.

5. The catalyst was a platinum divinyltetramethyldisiloxane complex containing about one weight percent of platinum carried in a solvent, i.e., Karstedt's catalyst.

6. The α-olefin was a $C_{18}$ α-olefin having the formula $CH_2=CH(CH_2)_{15}CH_3$.

An elastomeric silicone polymer was prepared by adding the ≡SiH siloxane, the mono-alkenyl polyether, and 84–95 percent by weight of the oil, i.e., decamethylcyclopentasiloxane, to the ESCO EL-1 processor mixer. After loading the materials into the mixer container, the mixer was closed. Heating of the mixer was initiated by setting the circulatory bath set point to about 70° C. The speed of the sweep blade of the mixer was activated to about 25–30 percent of its full capacity, and the speed of the homogenizer of the mixer was activated to about 5 percent of its full capacity. The platinum catalyst was added to the mixer via a syringe inserted through the port hole of the mixer, and the timer was started. Mixing was continued for about 30 minutes. The α-olefin was then added, and mixing of the contents in the container was continued for a minimum of another 15 minutes. Using an analytical balance, the α,ω-unsaturated hydrocarbon, i.e., 1,5-hexadiene, was weighed into a one ounce vial along with 10–20 g of the oil, and the vial was capped. The remaining portion of the oil was weighed and placed in a beaker.

Because of the volatility characteristics of 1,5-hexadiene, care was taken when adding it to the reaction mixture. The homogenizer was turned off, and the speed of the scraper was reduced to about 5 percent of its full capacity. The inlet plug of the ESCO processor mixer was removed, and a funnel with an extended stem, was inserted into the port hole of the inlet, so that the stem reached below the surface of the liquid in the container. The α,ω-unsaturated hydrocarbon, i.e., 1,5-hexadiene, was mixed with a portion of the oil, and poured into the funnel, followed by the addition of the remaining portion of the oil. When the contents in the funnel had been added, the funnel was removed, the inlet was closed, and the timer was restarted.

The speed of the scraper blade was increased to 15–20 percent of its full capacity, and the speed of the homogenizer was increased to 5 percent of its full capacity. The fluid in the mixer container began forming a gel, evidenced by material in the container thickening and climbing up the shaft of the mixer. The time of this occurrence of gelation was noted in a log book, and mixing of the contents was continued. The speeds of both the homogenizer and the scraper were reset to 10–15 percent of their full capacity, depending upon the rigidity of the gel present in the container. The total time of mixing measured from the point of addition of the platinum catalyst was a minimum of 3 hours at a constant temperature of about 70° C. At the end of this time, the set point of the mixer circulatory bath was lowered to 25° C., and mixing was continued. A post cure quenching agent was added, followed by dilution of the contents of the mixer container with the oil.

This procedure was used to prepare two silicone elastomeric polymers A and B, and the characteristics of each polymer are shown in Table 2. A silicone elastomer C was used for purposes of comparison, and it was prepared by a similar procedure, except that the mono-alkenyl polyether was omitted from the reaction mixture.

The following examples illustrate the use of silicone elastomers for preparing O/O and three-phase emulsions. The equipment used in these examples included 250 ml beakers, a Lightning brand L1-U08 digital mechanical mixer equipped with a high shear radial flow impeller having an impeller with four pitched blades spaced one centimeter from its center, and a Caframo brand RZR-50 mechanical mixer.

Example 2
Mineral Oil-in-Silicone Oil (O/O) Emulsion 42.5 gram of a 10 centistoke ($mm^2$/s) polydimethylsiloxane fluid was placed into a first beaker, and treated with a slight amount of an organosilicon fluorescent dye. The fluorescent dye was used to determine by analysis, which of the phases of the O/O emulsion was the external phase of the emulsion. The contents of the first beaker were then mixed by hand. Into a second beaker was added 15.0 gram of Emulsifier B and 42.5 gram of mineral oil. The mineral oil and Emulsifier B were then mixed together using a mechanical mixer at 500 rpm (52 rad/s) for about 5 minutes. Over a period of another 10 minutes, the fluorescent 10 centistoke ($mm^2$/s) polydimethylsiloxane fluid was added to the second beaker containing the mineral oil and Emulsifier B. When the addition was completed, the speed of the mechanical mixer was increased to about 800 rpm (84 rad/s), and the contents of the second beaker were mixed for another 30 minutes. By fluorescent analysis, it was determined that a mineral oil-in-silicone oil emulsion had been prepared.

Example 3
Mineral Oil/Water/Silicone Oil Three-Phase Emulsion 40.0 gram of deionized water was placed into a first beaker, and treated with a slight amount of calcein disodium salt fluorescent dye. The contents of the first beaker were then mixed by hand. Into a second beaker was placed 50.0 gram of the mineral oil-in-silicone oil emulsion prepared in Example 2. The contents of the second beaker were mixed with a mechanical mixer at 600 rpm (63 rad/s) for 5 minutes. Over a time interval of about 10 minutes, the treated water was added to the second beaker. When the addition was complete, the speed of the mechanical mixer was increased to 1300 rpm (136 rad/s), and mixing was continued for another 30 minutes. By fluorescent analysis, it was determined that a three-phase emulsion containing mineral oil and water dispersed in the silicone oil had been prepared. The emulsion was peach colored.

Example 4
Castor Oil-in-$D_5$ (O/O) Emulsion 20.0 gram of Emulsifier A swollen with $D_5$ was placed in a glass beaker and mixed with a mechanical mixer at 1300 rpm (136 rad/s). To the beaker was then added 18.58 gram of castor oil over a period of about 15 minutes. It resulted in a white castor oil-in-$D_5$ emulsion.

Example 5
Castor Oil/Water/$D_5$ Three-Phase Emulsion 20 gram of the castor oil-in-$D_5$ emulsion prepared in Example 4 was placed into a glass beaker and mixed with a mechanical mixer at 1300 rpm (136 rad/s). Over a period of about 15 minutes, to the beaker was added 27.17 gram of deionized water. The result was a thick, white, three-phase emulsion containing castor oil and water dispersed in $D_5$.

Example 6—Comparison Example
O/O Emulsion

Example 4 was repeated except that 20.0 gram of Emulsifier C swollen with Ds was placed in a glass beaker and mixed with a mechanical mixer at 600 rpm (63 rad/s). To the beaker was then added 16.84 gram of castor oil over a period of about 10 minutes. When addition was completed, the beaker contents were mixed for an additional 5 minutes. It resulted in a white castor oil-in-$D_5$ emulsion. However, this emulsion was not stable, and phase separation occurred. This comparison example shows the negative effect of omitting the polyether groups from the silicone elastomer.

A summary of these examples is shown in Table 1.

TABLE 1

| Example | Emulsifier | Oil (s) | Emulsifier gram | Oil gram | Water gram |
|---|---|---|---|---|---|
| 2 | B | 10 mm$^2$/s Silicone oil & Mineral Oil | 15 | 42.5 42.5 | — |
| 3 | B | — | 50 | — | 40 |
| 4 | A | Castor Oil & D$_5$ | 20 | 18.58 | — |
| 5 | A | — | 20 | — | 27.17 |
| 6 | C | Castor Oil & D$_5$ | 20 | 16.84 | — |

The characteristics of the silicone elastomers used as emulsifiers in these examples is shown in Table 2.

TABLE 2

| | | Elastomers Prepared in Example 1 | | | |
|---|---|---|---|---|---|
| Silicone Elastomer | Olefin Group | Equivalents of ≡SiH taken up by olefin | Ethylene Oxide (EO) Unit | Equivalents of ≡SiH taken up by EO unit | # of Cross Links |
| A | C$_{18}$ | 13 | 12 | 2 | 5 |
| B | C$_{18}$ | 13 | 7 | 2 | 5 |
| C | C$_{16}$ | 20 | 0 | 0 | 4 |

The ≡SiH siloxane copolymer used in Example 1, i.e., Me$_3$SiO(Me$_2$SiO)$_{77}$(MeHSiO)$_{20}$SiMe$_3$, had twenty (20) reactive sites available for reaction with sites in other components of the reaction mixture, and/or for crosslinking with sites in other molecules. In Table 2, and using Silicone Elastomeric Polymer A as an example, it can be seen that 13 equivalents of the ≡SiH reactive sites in the copolymer were taken up by the olefin portion of the polymer, and 2 equivalent of the ≡SiH reactive sites in the copolymer were taken up by the ethylene oxide portion of the polymer. The remaining 5 equivalents of the total of 20 equivalents of ≡SiH reactive sites available in the copolymer were taken up in crosslinking with 1,5-hexadiene, which occurred between and among the molecules in forming the gelled three-dimensional network.

Other types of reactive compositions can be used to prepare the elastomeric silicone polymer without departing from the spirit of the invention. For example, one can prepare elastomeric silicone polymers by reacting the mono-alkenyl polyether and the α-olefin with the following other types of reactive compositions, instead of using the particular ≡Si—H containing polysiloxanes and α,ω-unsaturated hydrocarbons described above:

ZMe$_2$SiO(Me$_2$SiO)$_r$(MeHSiO)$_s$SiMe$_2$Z and
QMe$_2$SiO(Me$_2$SiO)$_t$(MeQSiO)$_u$SiMe$_2$Q where Me is methyl; Z is CH$_3$ or H provided there are at least two H atoms per molecule; Q is vinyl or another alpha-unsaturated alkenyl group or CH$_3$ provided there are at least two carbon-carbon double bonds per molecule; r is 0–1,000; s is 0–100; t is 0–1,000; and u is 0–100.

One can also prepare elastomeric silicone polymers by reacting the mono-alkenyl polyether and α-olefin with the following types of reactive compositions, instead of using the particular ≡Si—H containing polysiloxanes and α,ω-unsaturated hydrocarbons described above:

(RMe$_2$SiO$_{1/2}$)$_v$(SiO$_{4/2}$)$_w$(RSiO$_{3/2}$)$_x$(RMeSiO$_{2/2}$)$_y$ and
QMe$_2$SiO(Me$_2$SiO)$_z$(MeQSiO)$_λ$SiMe$_2$Q where Me is methyl; R is methyl or H provided there are at least two H atoms per molecule; Q is vinyl or another alpha-unsaturated alkenyl group or methyl provided there are at least two carbon—carbon double bonds per molecule; v is 2–50; w is 0–20; x is 0–50; y is 0–1,000; z is 0–1,000; and λ is 0–100.

The emulsions described in this invention have particular value in the personal care arena. They can be used alone, or blended with other cosmetic ingredients, to form a variety of over-the-counter (OTC) personal care products.

Thus, they are useful as carriers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, and provide conditioning benefits.

In cosmetics, they can function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, the compositions can impart a dry, silky-smooth, payout.

In addition, the emulsion compositions exhibit other advantageous and beneficial properties such as shelf stability and ease of preparation. Hence, they can have wide application, but especially in antiperspirants, deodorants, skin care products, and for conditioning hair.

Further, the emulsion compositions are capable of functioning as carriers for pharmaceuticals, biocides, herbicides, pesticides, and other biologically active substances.

Finally, the emulsion compositions have utility as additives for cellulosic or synthetic nonwoven carrier substrates used in wet-like cleansing wipes such as wet-wipes, tissues, and towels, marketed generally for personal hygiene and household cleaning tasks.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising an oil-in-oil emulsion in which one oil phase of the oil-in-oil emulsion is a silicone oil, and the other oil phase of the oil-in-oil emulsion is an organic oil, the oil phases being mutually insoluble and being emulsified using as the emulsifier, an elastomeric silicone polymer having (i) dimethyl, (ii) C10 or higher alkyl, (iii) polyether, and (iv) crosslinking groups in its molecule; the elastomeric silicone polymer being prepared by combining and reacting:

(A) an =Si—H containing polysiloxane of the formula R$_3$SiO(R'$_2$SiO)$_a$(R"HSiO)$_b$SiR$_3$, or the formula (R'$_2$SiO)$_{a'}$(R"HSiO)$_{b'}$, or the formula HR$_2$SiO(R'$_2$SiO)$_c$SiR$_2$H, or the formula HR$_2$SiO (R'$_2$SiO)$_a$(R"HSiO)$_b$SiR$_2$H, where R, R', and R" are alkyl groups with 1–6 carbon atoms, a is 0–250, a' is 0–7, b is 1–250, b' is 3–10, and c is 0–250;

(B) a mono-alkenyl polyether of the formula CH$_2$=CH (CH$_2$)$_f$O(CH$_2$CH$_2$O)$_g$(CH$_2$CH$_3$CHO)$_h$T, or the formula CH$_2$=CH—Q—O(CH$_2$CH$_2$O)$_g$(CH$_2$CH$_3$CHO)$_h$T, where T is hydrogen, a C$_1$–C$_{10}$ alkyl group, an aryl group, or a C$_{1-C20}$ acyl group; Q is a divalent linking group containing unsaturation; f is 0–6, g is 4–100; and h is zero or 1–100;

(C) an α-olefin containing at least ten carbon atoms;

(D) an α,ω-unsaturated hydrocarbon selected from the group consisting of α,ω-dienes of the formula $CH_2=CH(CH_2)_dCH=CH_2$, α,ω-diynes of the formula $CH\equiv C(CH_2)_eC\equiv CH$, and α,ω-ene-ynes of the formula $CH_2=CH(CH_2)_eC\equiv CH$, where d is 1–20 and e is 0–20; and (E) a platinum catalyst; in the presence of (F) a silicone oil;

and allowing the reaction to continue until there is formed a crosslinked three-dimensional gelled network of an elastomeric silicone polymer.

2. A composition according to claim 1 in which the silicone oil comprises the continuous phase of the emulsion and the silicone oil has a viscosity of 0.65 to about 1,000 $mm^2/s$.

3. A composition according to claim 1 in which the organic oil is a natural oil derived from animal, vegetable, or mineral sources.

4. A composition according to claim 3 in which the organic oil is selected from the group consisting of almond oil, apricot kernel oil, avocado oil, cacao butter, carrot oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark oil, soybean oil, sweet almond oil, tallow oil, tallow oil, turtle oil, vegetable oil, whale oil, and wheat germ oil.

5. A method of treating hair, skin, or underarm comprising applying to the hair, skin, or underarm, the composition according to claim 1.

6. A method of treating cellulosic or synthetic nonwoven carrier substrates comprising applying to cellulosic or synthetic nonwoven carrier substrates the composition according to claim 1.

7. A composition comprising a three-phase emulsion in which one phase of the three-phase emulsion is a silicone oil, another phase of the three-phase emulsion is an organic oil, and a third phase of the three-phase emulsion is water, the oil phases and the water being mutually insoluble and being emulsified using as the emulsifier, an elastomeric silicone polymer having (i) dimethyl, (ii) C10 or higher alkyl, (iii) polyether, and (iv) crosslinking groups in its molecule; the elastomeric silicone polymer being prepared by combining and reacting:

(A) an ≡Si—H containing polysiloxane of the formula $R_3SiO(R'_2SiO)_a(R''HSiO)_bSiR_3$, or the formula $(R'_2SiO)_{a'}(R''HSiO)_{b'}$, or the formula $HR_2SiO(R'_2SiO)_cSiR_2H$, or the formula $HR_2SiO(R'_2SiO)_a(R''HSiO)_bSiR_2H$, where R, R', and R" are alkyl groups with 1–6 carbon atoms, a is 0–250, a' is 0–7, b is 1–250, b' is 3–10, and c is 0–250;

(B) a mono-alkenyl polyether of the formula $CH_2=CH(CH_2)_fO(CH_2CH_2O)_g(CH_2CH_3CHO)_hT$, or the formula $CH_2=CH—Q—O(CH_2CH_2O)_g(CH_2CH_3CHO)_hT$, where T is hydrogen, a $C_1–C_{10}$ alkyl group, an aryl group, or a $C_1–C_{20}$ acyl group; Q is a divalent linking group containing unsaturation; f is 0–6, g is 4–100; and h is zero or 1–100;

(C) an α-olefin containing at least ten carbon atoms;

(D) an α,ω-unsaturated hydrocarbon selected from the group consisting of α,ω-dienes of the formula $CH_2=CH(CH_2)_dCH=CH_2$, α,ω-diynes of the formula $CH\equiv C(CH_2)_eC\equiv CH$, and α,ω-ene-ynes of the formula $CH_2=CH(CH_2)_eC\equiv CH$, where d is 1–20 and e is 0–20; and (E) a platinum catalyst; in the presence of (F) a silicone oil;

and allowing the reaction to continue until there is formed a crosslinked three-dimensional gelled network of an elastomeric silicone polymer.

8. A composition according to claim 7 in which the silicone oil comprises the continuous phase and the silicone oil has a viscosity of 0.65 to about 1,000 $mm^2/s$.

9. A composition according to claim 7 in which the organic oil is a natural oil derived from animal, vegetable, or mineral sources.

10. A composition according to claim 9 in which the organic oil is selected from the group consisting of almond oil, apricot kernel oil, avocado oil, cacao butter, carrot oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark oil, soybean oil, sweet almond oil, tallow oil, tallow oil, turtle oil, vegetable oil, whale oil, and wheat germ oil.

11. A method of treating hair, skin, or underarm comprising applying to the hair, skin, or underarm, the composition according to claim 9.

12. A method of treating cellulosic or synthetic nonwoven carrier substrates comprising applying to cellulosic or synthetic nonwoven carrier substrates the composition according to claim 7.

* * * * *